United States Patent
Kankan et al.

(10) Patent No.: US 8,383,627 B2
(45) Date of Patent: Feb. 26, 2013

(54) CRYSTALLINE POLYMORPH OF DOXAZOSIN MESYLATE (FORM IV) AND PROCESS FOR PREPARATION THEREOF

(75) Inventors: Rajendra Narayanrao Kankan, Maharashtra (IN); Dharmaraj Ramachandra Rao, Maharashtra (IN); Manish Gopaldas Gangrade, Maharashtra (IN); Shrikant Suresh Mudgal, Maharashtra (IN)

(73) Assignee: CIPLA Limited, Mumbai (IN)

( * ) Notice: Subject to any disclaimer, the term of this patent is extended or adjusted under 35 U.S.C. 154(b) by 375 days.

(21) Appl. No.: 12/810,297

(22) PCT Filed: Jul. 10, 2008

(86) PCT No.: PCT/GB2008/002362
§ 371 (c)(1),
(2), (4) Date: Sep. 27, 2010

(87) PCT Pub. No.: WO2009/081087
PCT Pub. Date: Jul. 2, 2009

(65) Prior Publication Data
US 2011/0034477 A1    Feb. 10, 2011

(30) Foreign Application Priority Data
Dec. 24, 2007  (IN) .................... 2537/MUM/2007

(51) Int. Cl.
*A61K 31/497* (2006.01)
*C07D 239/02* (2006.01)

(52) U.S. Cl. ................ 514/252.17; 544/294
(58) Field of Classification Search .......... None
See application file for complete search history.

(56) References Cited

U.S. PATENT DOCUMENTS
6,500,830 B1   12/2002   Klein et al.
2002/0065287 A1   5/2002   Giridhar et al.

FOREIGN PATENT DOCUMENTS
| | | |
|---|---|---|
| CA | 2224884 A1 | 6/1998 |
| CA | 2224916 | 6/1998 |
| CA | 2225022 C | 10/2008 |
| EP | 0848001 A1 | 6/1998 |
| EP | 0849264 A1 | 6/1998 |
| EP | 0849266 A1 | 6/1998 |
| WO | 9935143 A1 | 7/1999 |
| WO | 0056731 A1 | 9/2000 |
| WO | 2009081087 A1 | 7/2009 |

OTHER PUBLICATIONS

Chinese Journal of Medicinal Chemistry, vol. 5, No. 4, pp. 266-270, Dec. 1995.
Foreign communication from the priority application—International Search Report and Written Opinion, PCT/GB2008/002362, Nov. 26, 2008, 17 pages.
Foreign communication from the priority application—International Preliminary Report on Patentability, PCT/GB2008/002362, Jun. 29, 2010, 8 pages.
Goho, Alexandra, "Tricky Business: The crystal form of a drug can be the secret to its success," Science News, vol. 166, pp. 122-124, Aug. 21, 2004.
Greman, M., et. al., "Study of Polymorphism of 1-(4-amino-6,7-dimethoxy-2-quinazolinyl)-4-[(2,3-dihydro-1,4-benzodioxin-2-yl)carbonyl]-piperazine monomethanesulfonate," Farmacevtski vestnik, 1997, vol. 48, pp. 292-293.
Haleblian, John K., "Characterization of Habits and Crystalline Modification of Solids and Their Pharmaceutical Applications," Journal of Pharmaceutical Sciences, vol. 64, No. 8, Aug. 1975.
Haleblian, John K., et al., "Pharmaceutical Applications of Polymorphism," Journal of Pharmaceutical Sciences, vol. 58, No. 8, Aug. 1969.
Sohn, Young-Taek, et al., "Effect of Crystal Form on in Vivo Topical Anti-Inflammatory Activity of Corticosteroids," Arch. Pharm. Res., vol. 25, No. 4, pp. 556-559, 2002.
Sohn, Young-Taek, et al., "Polymorphism of Doxazosin Mesylate," Arch. Pharm. Res., vol. 28, No. 6, pp. 730-735, 2005.

*Primary Examiner* — James O Wilson
*Assistant Examiner* — Oluwafemi Masha
(74) *Attorney, Agent, or Firm* — Conley Rose, P.C.; Rodney B. Carroll (57) ABSTRACT

Crystalline Form IV of doxazosin mesylate, a process for its preparation and uses thereof.

15 Claims, 4 Drawing Sheets

CRYSTALLINE POLYMORPH OF DOXAZOSIN MESYLATE (FORM IV) AND PROCESS FOR PREPARATION THEREOF

CROSS-REFERENCE TO RELATED APPLICATIONS

This application is a filing under 35 U.S.C. 371 of International Application No. PCT/GB2008/002362 filed Jul. 10, 2008, entitled "Crystalline Polymorph of Doxazosin Mesylate (Form IV) and Process for Preparation Thereof," claiming priority of Indian Patent Application No. 2537/MUM/2007 filed Dec. 24, 2007, which applications are incorporated by reference herein in their entirety.

FIELD OF INVENTION

The present invention relates to a novel crystalline form of 1-(4-amino-6,7-dimethoxy-2-quinazolinyl)-4-(2,3-dihydro-1,4-benzodioxin-2-yl)carbonyl piperazine monomethanesulfonate, also known as doxazosin mesylate. More specifically, the invention relates to novel Form IV of doxazosin mesylate, methods for preparing the novel form of doxazosin mesylate and pharmaceutical formulations comprising the novel form of doxazosin mesylate. The structure of doxazosine is shown below.

BACKGROUND OF THE INVENTION

Pharmaceutical solids can exist in different crystal forms, such as crystalline, amorphous, or glass and also in solvated or hydrated states (Haleblian et al., 1969, 1975; Kuhnert-Brandstaetter, 1973; Sohn 2004). Polymorphism is the ability of any element or compound to crystallize as more than one distinct crystal species.

It is a well known fact that different polymorphic forms of the same drug may have substantial differences in certain pharmaceutically-important physicochemical properties, such as stability, solubility, dissolution rate, crystal habit, tableting behavior. Changes in certain of these physiochemical properties may ultimately affect the bioavailability of the drug. Furthermore, different physical forms may have different particle size, hardness and glass transition temperatures.

Regulatory authorities desire to have all possible polymorphic forms of a new drug substance identified prior to approval of a product containing the drug. However, as is well known in the art, the existence of polymorphic forms of any given compound cannot be predicted, and there is no standard procedure for proceeding to make a previously unknown polymorphic form. Even after a polymorph has been identified, there is no possibility of predicting whether any additional forms will ever be discovered. This has been described in many recent articles, including A. Goho, *Science News*, Vol. 166, No. 8, pages 122-123 (August 2004).

Doxazosin mesyalte is a quinazoline compound, that is a selective inhibitor of the α-1 subtype of α-adrenergic receptors. It is known to be useful in men to treat the symptoms of an enlarged prostate (benign prostatic hyperplasia or BPH), which include difficulty urinating (hesitation, dribbling, weak stream, and incomplete bladder emptying), painful urination, and urinary frequency and urgency. Doxazosin (Cardura) is also used alone or in combination with other medications to treat high blood pressure. Doxazosin is in a class of medications called alpha-blockers. It relieves the symptoms of BPH by relaxing the muscles of the bladder and prostate. It lowers blood pressure by relaxing the blood vessels so that blood can flow more easily through the body.

Literature data show that the doxazosin mesylate exists in different crystalline polymorphic forms.

The Chinese Journal of Medicinal Chemistry (1995, 5:266-270) described for the first time three crystal forms: Form A, Form B and Form C.

Subsequently, M. Greman et al. (Farmacevtski vestnik, 1997, 48: 292-293) described five different forms, namely A, B, C, D, and E of doxazosin mesylate.

Grafe and Morsdorf (CA 02224884, CA 0224916, CA 0222022) disclose methods of preparation of doxazosin mesylate forms which do not correspond to the polymorphic form of the present invention.

WO99/35143 and WO00/56731 claim processes for preparing Form A.

US 2002/0065287 A1 (Giridher et al.) describes two crystal forms A and D.

EP 849264, EP 849265 and EP 849266 disclose three crystalline forms of doxazosin mesylate Form I, Form II and Form III respectively.

Young-Taek Soh and Yoon-Hee Lee in Arch Pharm Res Journal (Vol 28, No. 6. 730-735, 2005) have recently described nine forms of doxazosin mesylate. The XRD patterns of nine doxazosin mesyalte forms are different from those previously reported in the literature.

Consequently, it would be a significant contribution to the art to provide a crystalline form of doxazosin mesylate, having increased solubility, and methods of preparation, pharmaceutical formulations, and methods of use thereof.

SUMMARY OF THE INVENTION

The present invention provides a novel crystalline form of doxazosin mesylate designated as Form IV, methods of preparing the novel form and pharmaceutical composition containing it. The advantages of the process include simplicity, eco-friendliness and suitability for commercial use.

The invention relates to a crystalline doxazosin mesylate Form IV. Thus, according to a first aspect of the present invention, there is provided Crystalline Form IV of doxazosin mesylate.

In an embodiment, the crystalline Form IV of doxazosin mesylate is characterized by having an XRD pattern comprising peaks at 7.1, 11.8 and 13.9°2θ±0.2°2θ. The XRD pattern may comprise further peaks at 15.9 and 22.3°2θ±0.2°2θ. The XRD pattern comprise still further peaks at 9.3 and 24.2°2θ±0.2°2θ. The XRD pattern may comprise yet further peaks at 17.3 and 23.7°2θ±0.2°2θ.

In an embodiment, crystalline polymorph Form IV of doxazosin mesylate is characterized by having an XRD pattern comprising peaks at 7.1, 9.3, 11.8, 13.9, 15.9, 22.3 and 24.2°2θ±0.2°2θ.

Figure 1:
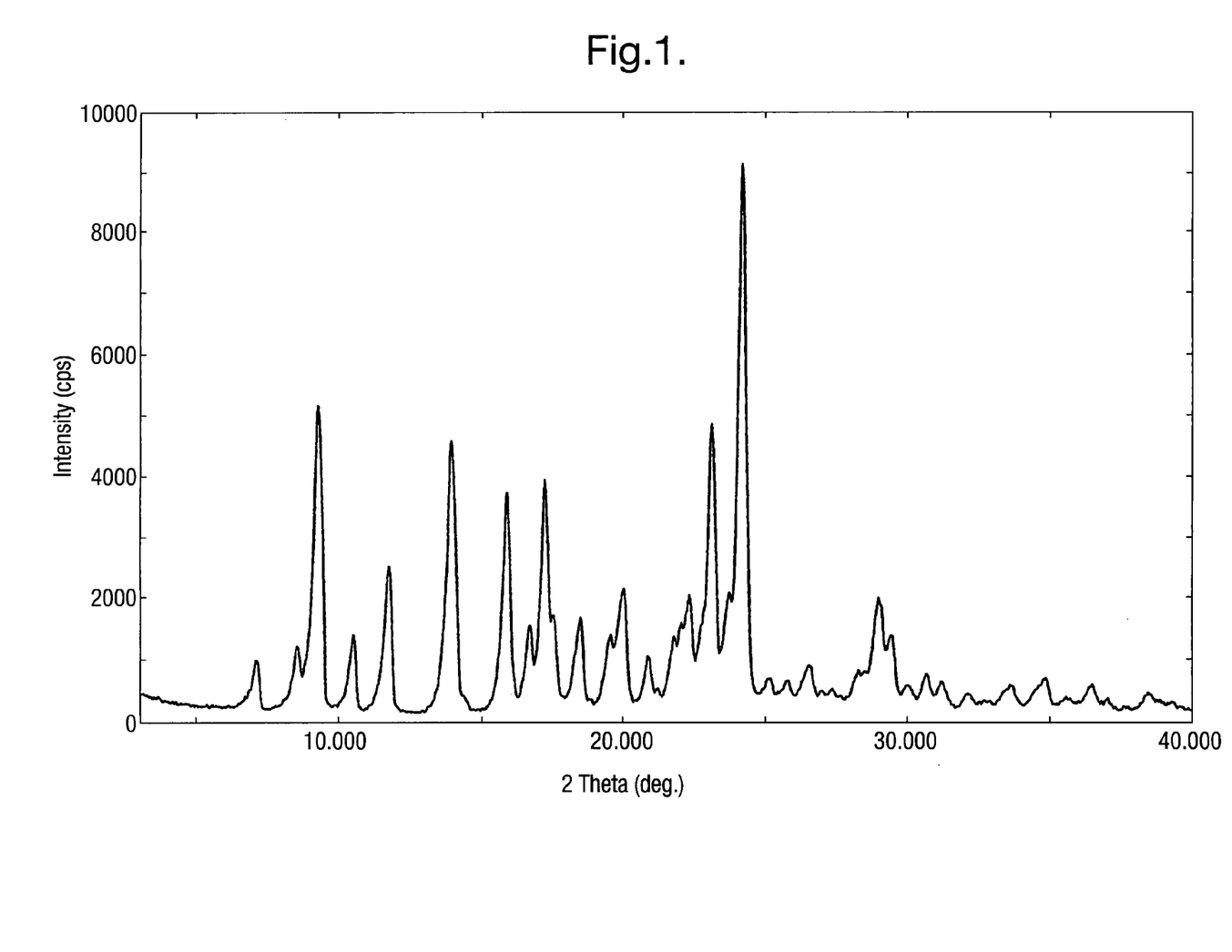
FIG. 1 is the X-ray powder diffractogram (XRD) of crystalline doxazosin mesylate Form IV of the present invention.

In another embodiment, crystalline Form IV of doxazosin mesylate is characterized by having an XRD pattern as shown in FIG. 1.

Crystalline Form IV of doxazosin mesylate may also be characterized by having an IR spectrum comprising characteristic IR spectra peaks at about 3345 cm$^{-1}$, 3185 cm$^{-1}$, 3033 cm$^{-1}$, 2934 cm$^{-1}$, 1660 cm$^{-1}$, 1635 cm$^{-1}$, 1597 cm$^{-1}$, 1533 cm$^{-1}$, 1492 cm$^{-1}$, 1469 cm$^{-1}$, 1438 cm$^{-1}$, 1397 cm$^{-1}$, 1317 cm$^{-1}$, 1262 cm$^{-1}$, 1236 cm$^{-1}$, 1215 cm$^{-1}$, 1183 cm$^{-1}$, 1112 cm$^{-1}$, 1046 cm$^{-1}$, 989.9 cm$^{-1}$, 927 cm$^{-1}$, 869 cm$^{-1}$, 846 cm$^{-1}$, 819 cm$^{-1}$, 771 cm$^{-1}$, 756 cm$^{-1}$, 720 cm$^{-1}$, 663 cm$^{-1}$, 628 cm$^{-1}$, 575 cm$^{-1}$, 553 cm$^{-1}$, 522 cm$^{-1}$, 453 cm$^{-1}$ and 433 cm$^{-1}$±2 cm$^{-1}$.

Figure 2:
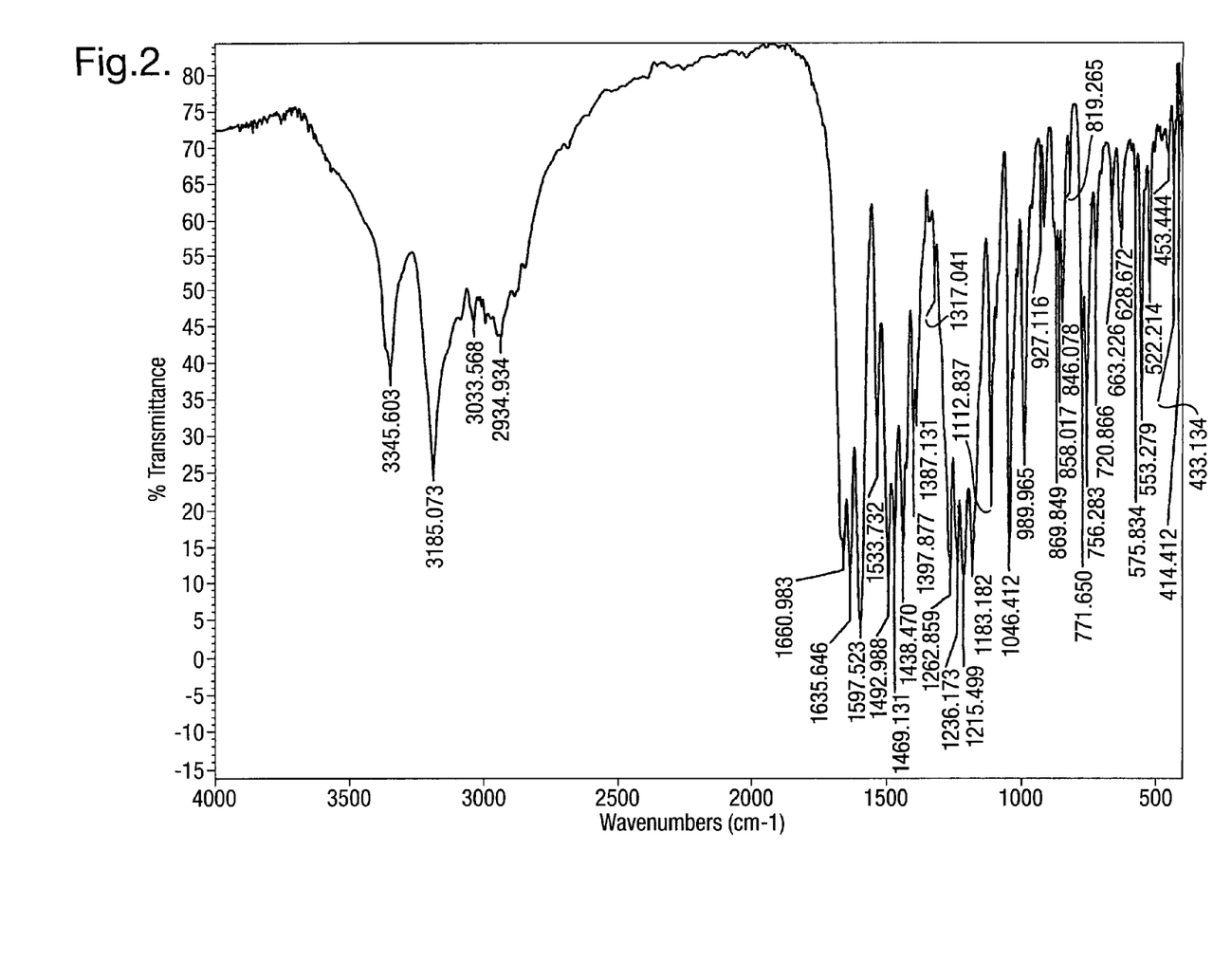
FIG. 2 is an Infra-Red (IR) absorption spectrum of crystalline doxazosin mesylate Form IV of the present invention.

In an embodiment, crystalline Form IV of doxazosin mesylate is characterized by having an IR spectrum as shown in FIG. 2.

Crystalline Form IV of doxazosin mesylate may also be characterised as having a DSC spectrum exhibiting a significant peak at around 258° C.

Figure 3:
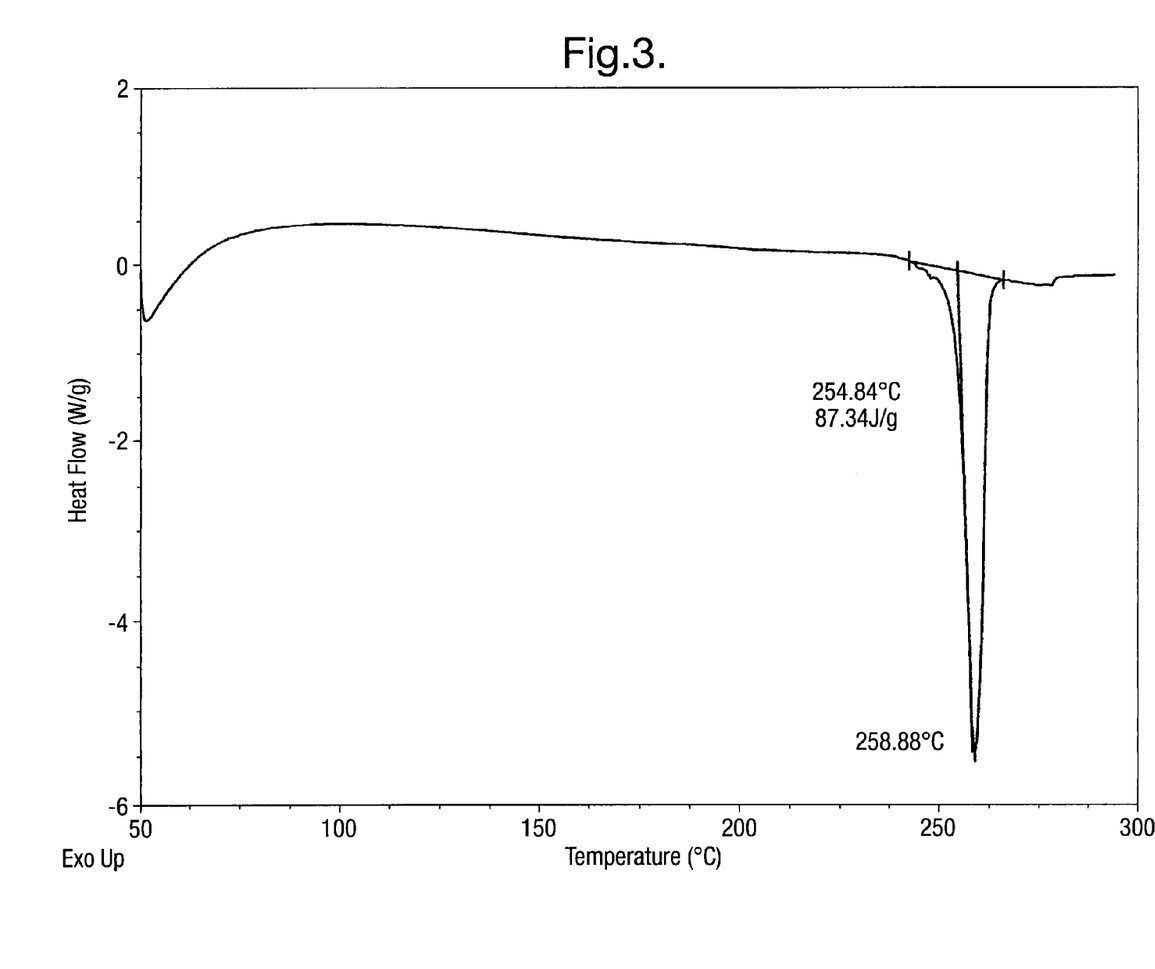
FIG. 3 is a Differential Scanning calorimetry (DSC) thermogram of crystalline doxazosin mesylate Form IV of the present invention.

In an embodiment, crystalline Form IV of doxazosin mesylate is characterized by having a DSC spectrum as shown in FIG. 3.

Figure 4:
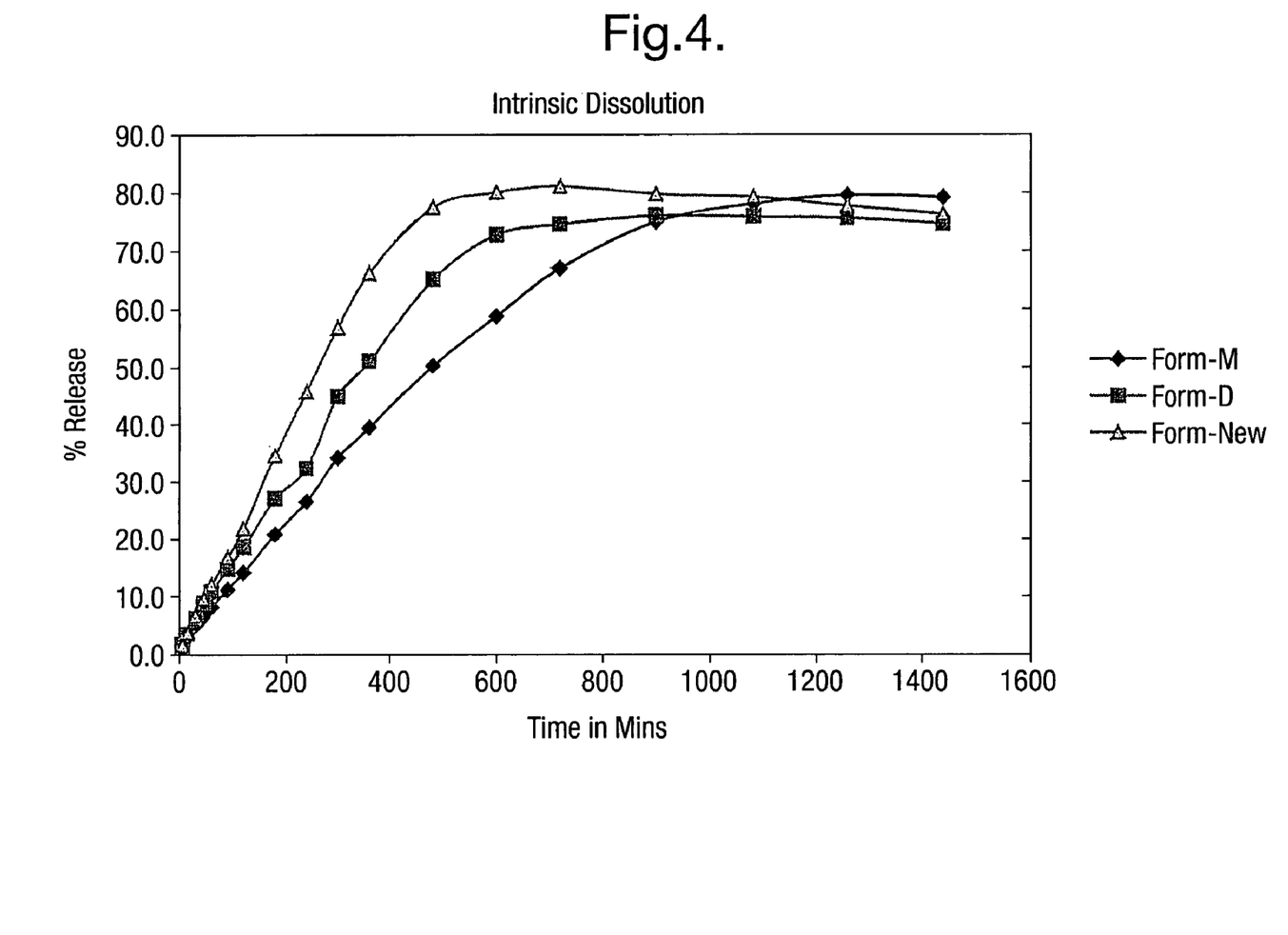
FIG. 4 is the Intrinsic Dissolution Profile of doxazosin mesylate Form IV of the present invention compared with that of prior art forms D and M of doxazosin mesylate by an HPLC-UV method.

In another embodiment, crystalline Form IV of doxazosin mesylate is characterized by having an intrinsic dissolution profile as shown in FIG. 4.

According to another aspect of the present invention, there is provided a process for preparing crystalline Form IV of doxazosin mesylate, the process comprising dissolving doxazosin base and methane sulfonic acid in a polar aprotic solvent, stirring the reaction mass for a period of time ranging from about 30 minutes to about 5 hours at a temperature ranging from about 25° C. to boiling point of the solvent, cooling the reaction mass to a temperature ranging from about 20° C. to 30° C. and stiffing for a period of time ranging from about 30 minutes to about 2 days, and isolating the precipitated crystalline Form IV of doxazosin mesylate. The crystalline Form IV of doxazosine mesylate prepared by the process may be as described above.

The doxazosine base may be in any polymorphic form or in a mixture of any polymorphic forms.

In an embodiment, the solvent is selected from methanol, tetrahydrofuran, acetone, 1,4-dioxane, dimethylformamide, dimethylsulfoxide and N-methyl-2-pyrrolidone. Preferably the solvent is acetone or methanol.

In the first stirring step, the reaction mass may be stirred at a temperature ranging from about 25° C. to about 40° C., at a temperature ranging from about 30° C. to about 40° C.

In the second stiffing step, the stiffing may be for a period of time ranging from 1 hour to 2 days.

According to another aspect of the present invention, there is provided crystalline Form IV of doxazosin mesylate prepared by a process according to the process described above.

According to another aspect of the present invention, there is provided a pharmaceutical composition comprising crystalline Form IV of doxazosin mesylate as described above, together with one or more pharmaceutically acceptable excipients.

Suitably, the pharmaceutical composition is in the form of a tablet suitable for oral delivery.

According to another aspect of the present invention, there is provided crystalline Form IV of doxazosin mesylate as described above for use in medicine.

According to another aspect of the present invention, there is provided crystalline Form IV of doxazosin mesylate as described above for use in treating hypertension or benign prostatic hyperplasia.

According to another aspect of the present invention, there is provided the use of crystalline Form IV of doxazosin mesylate as described above for use in the manufacture of a medicament for treating hypertension or benign prostatic hyperplasia.

According to another aspect of the present invention, there is provided a method of treating hypertension or benign prostatic hyperplasia comprising administering to a patient in need thereof a therapeutically effective amount of crystalline Form IV of doxazosin mesylate as described above.

DETAILED DESCRIPTION

In one aspect, the present invention provides a stable crystalline polymorph of doxazosin mesylate which is substantially non-hygroscopic and has good flow characteristics. In particular, the Form IV of doxazosin mesylate has superior intrinsic dissolution, particularly compared to prior art forms of doxazosin mesylate.

In another aspect, the present invention provides a process for preparing the novel form of doxazosin mesylate designated as Form IV. In an embodiment, the process is solvate-free. The present invention also provides pharmaceutical compositions comprising Form IV of doxazosin mesylate.

The process produces Form IV of doxazosin mesylate in high yield and purity.

In an embodiment, the process involves isolation of the Form IV of doxazosin mesylate in a solvent-free media, thus producing doxazosin mesylate free of solvents or having a negligible solvent content. In an embodiment, the solvent content of the Form IV of doxazosin mesylate is not more than 8000 parts per million (ppm). Typically, the methanol content is not more than 3000 ppm and preferably is around 69 ppm maximum. Typically, the acetone content is not more than 5000 ppm and preferably is around 254 ppm maximum.

The crystalline nature of Form IV of doxazosin mesylate has been analyzed, characterized and differentiated by X-ray powder diffraction, a technique which is known per se.

The X-ray powder diffraction pattern of crystalline polymorph Form IV of doxazosin mesylate was measured on a Rigaku Dmax 2200 advanced X-ray powder diffractometer with a copper-K-α radiation source.

In an embodiment, the crystalline polymorph Form IV of doxazosin mesylate has an XRD pattern comprising peaks at 7.1, 11.8 and 13.9°2θ±0.2°2θ. The crystalline polymorph Form IV of doxazosin mesylate may have an XRD pattern comprising further peaks at 15.9 and 22.3°2θ±0.2°2θ. Thus, typically, the crystalline polymorph Form IV of doxazosin mesylate has an XRD pattern comprising peaks at 7.1, 11.8, 13.9, 15.9 and 22.3°2θ±0.2°2θ. The crystalline polymorph Form IV of doxazosin mesylate may have an XRD pattern comprising further peaks at 9.3 and 24.2°2θ±0.2°2θ. The crystalline polymorph Form IV of doxazosin mesylate may have an XRD pattern comprising still further peaks at 17.3 and 23.7°2θ±0.2°2θ. Thus, in a further embodiment, the crystalline polymorph Form IV of doxazosin mesylate has an XRD pattern comprising peaks at 7.1, 9.3, 11.8, 13.9, 15.9, 22.3 and 24.2°2θ±0.2°2θ.

In an embodiment, the crystalline polymorph Form IV of doxazosin mesylate has an XRD pattern with peaks at 2θ-values as shown in Table 1.

TABLE 1

XRD Peaks

| Diffraction angle (2θ-values) | Intensity (%) |
| --- | --- |
| 7.062 | 7.5 |
| 8.540 | 13.7 |
| 9.300 | 56.6 |
| 10.501 | 9.7 |
| 11.760 | 22.9 |
| 13.901 | 52.0 |
| 15.879 | 36.4 |
| 16.700 | 9.2 |
| 17.259 | 42.5 |
| 17.520 | 29.7 |
| 18.500 | 12.0 |
| 19.540 | 19.4 |
| 20.018 | 27.0 |
| 20.899 | 5.3 |
| 21.779 | 15.7 |
| 22.040 | 22.4 |
| 22.338 | 27.0 |
| 22.723 | 5.1 |
| 23.139 | 30.2 |
| 23.720 | 43.9 |
| 24.219 | 100.0 |
| 26.539 | 4.4 |
| 28.144 | 3.5 |
| 28.258 | 3.5 |
| 28.460 | 5.6 |
| 28.921 | 29.7 |
| 29.438 | 20.0 |
| 30.679 | 4.1 |
| 31.181 | 3.7 |
| 33.380 | 3.7 |
| 33.619 | 3.8 |
| 34.423 | 5.1 |
| 34.859 | 5.4 |
| 36.479 | 3.6 |
| 38.439 | 3.3 |
| 38.877 | 3.6 |

In another embodiment, doxazosin mesylate Form IV of the present invention is characterized by having an X-ray powder diffraction spectrum as shown in FIG. 1.

Infrared (FT-IR) spectra were obtained in a KBr disk using a Perkin Elmer FT-IR spectrophotometer Spectrum 1000 at resolution 4 $cm^{-1}$. The characteristic absorption bands are expressed in $cm^{-1}$.

In an embodiment, doxazosin mesylate Form IV of the present invention is characterized by having characteristic IR spectra peaks at about 3345 $cm^{-1}$, 3185 $cm^{-1}$, 3033 $cm^{-1}$, 2934 $cm^{-1}$, 1660 $cm^{-1}$, 1635 $cm^{-1}$, 1597 $cm^{-1}$, 1533 $cm^{-1}$, 1492 $cm^{-1}$, 1469 $cm^{-1}$, 1438 $cm^{-1}$, 1397 $cm^{-1}$, 1317 $cm^{-1}$, 1262 $cm^{-1}$, 1236 $cm^{-1}$, 1215 $cm^{-1}$, 1183 $cm^{-1}$, 1112 $cm^{-1}$, 1046 $cm^{-1}$, 989.9 $cm^{-1}$, 927 $cm^{-1}$, 869 $cm^{-1}$, 846 $cm^{-1}$, 819 $cm^{-1}$, 771 $cm^{-1}$, 756 $cm^{-1}$, 720 $cm^{-1}$, 663 $cm^{-1}$, 628 $cm^{-1}$, 575 $cm^{-1}$, 553 $cm^{-1}$, 522 $cm^{-1}$, 453 $cm^{-1}$ and 433 $cm^{-1}$.

In another embodiment, doxazosin mesylate Form IV of the present invention is characterized by having an IR spectrum as shown in FIG. 2.

In an embodiment, doxazosin mesylate Form IV of the present invention is characterized as having a DSC, exhibiting a significant peak at around 258° C. In another embodiment, doxazosin mesylate Form IV of the present invention is characterised as having a DSC as shown in FIG. 3.

In an embodiment, doxazosin mesylate Form IV of the present invention is characterized by having an intrinsic dissolution profile as shown in FIG. 4.

To measure the intrinsic dissolution of the doxazosin mesylate Form IV, Form M and Form D, samples were measured to compare the influence of the different parameter settings. At appropriate time intervals, an automated sample collector removes aliquots from dissolution medium for analysis. The time interval for sampling can vary, for example, from 2 to 30 minutes, depending on the properties of the drug and dissolution medium used. Suitable dissolution equipment for these operations include LAB INDIA DISSO 2000.

In another aspect, the present invention provides a process for the preparation of doxazosin mesylate Form IV. The doxazosin base used in preparing the polymorph may be obtained by methods described in the prior art which are herein incorporated by reference in their entirety. The doxazosin used as a starting material can be in any form, e.g. it can be in a reaction solution, suspension, crude or in anhydrous, hydrated or solvated form.

Form IV doxazosin mesylate may be prepared by dissolving doxazosin base of any form, or in a mixture of any forms, with methane sulfonic acid in an polar aprotic solvent. The reaction mass may be stirred for about 30 minutes to about 5 hours at a temperature of about 25° C. to boiling temperature of the solvent. The Form IV produced in the reaction solution may be isolated by cooling at around room temperature and stiffing for a prolonged time period. Examples of prolonged time periods include, but are not limited to, 30 minutes to a few hours, such as 2 hours, or to a few days, such as 2 days. In an embodiment, the second prolonged period is from about 1 hour to about days, preferably from about 1 hour to about 1 day, more preferably from about 1 hour to about 3 hours.

The solvent employed in this process are polar aprotic solvents and may be selected from tetrahydrofuran, acetone, 1,4-dioxane, dimethylformamide, dimethylsulfoxide and N-methyl-2-pyrrolidone. In a preferred embodiment the solvent is acetone.

The reaction is preferably performed at a temperature ranging from about 25° C. to about 40° C. Preferably, the reaction is performed at a temperature ranging from about 30 to about 40° C. Typically the reaction time ranges from about 2 to about 4 hours. The precipitated Form IV may be isolated by filtration, for example by either gravity or suction. The precipitate may be dried at room temperature and/or in vacuum to obtain Form IV.

The novel polymorph of doxazosin mesylate obtained according to the present invention is substantially free from other crystal and non-crystal forms of doxazosin mesylate. "Substantially free" from other forms of doxazosin mesylate shall be understood to mean that the polymorphs of doxazosin mesylate contain less than 10%, preferably less than 5%, of any other forms of doxazosin mesylate and less than 1% of other impurities, water or solvates. Thus, the doxazosine mesylate Form IV prepared according to the present invention contains less than 11% total impurities, preferably less than 6% total impurities. In a particularly preferred embodiment, the doxazosine mesylate Form IV prepared according to the present invention contains less than 1% total impurities. For example, the doxazosine mesylate Form IV prepared according to the processes described in Examples 1 and 2 below are 99.89% and 99.91%, respectively.

The process of invention may be used as a method for purifying any form of doxazosin mesylate, as well as for the preparation of the new polymorphic Form IV.

Doxazosin mesylate has been found to be effective for the control of elevated blood pressure (hypertension) and for benign prostatic hyperplasia (noncancerous enlargement of the prostate gland). Pharmaceutical compositions according to the present invention comprise Form IV doxazosin mesylate as an active ingredient together with one or more pharmaceutically acceptable carriers, excipients or diluents. Any conventional technique may be used for the preparation of pharmaceutical compositions according to the invention.

Pharmaceutical compositions may be formulated for oral delivery in the form of tablets. Pharmaceutical compositions according to the present invention may preferably comprise 1 mg, 2 mg, 4 mg, or 8 mg of active ingredient along with a pharmaceutically acceptable carrier. Doxazosin mesylate tablets of the present invention may be taken with or without food on the same time each day to maintain proper blood levels.

EXAMPLES

The invention is further described by reference to the following examples, which set forth in detail certain aspects and embodiments of the preparation of compounds and compositions of the present invention. It will be apparent to those skilled in the art, that many modifications, both to materials and methods, can be practiced without departing from the purpose and intent of this invention. The examples that follow are not intended to limit the scope of the invention as described herein above or as claimed below.

Example 1

Preparation of Doxazosin Mesylate Form IV

Doxazosin (100 gms) was charged in acetone (0.8 lit) at room temperature. The contents were stirred for 10 mins at 25-30° C. Methane sulfonic acid (23.2 ml) was charged slowly at 25-30° C. The reaction mass was heated at 35-38° C. and the temperature maintained for 2 hours. The reaction mass was cooled to 25-30° C. and stirred for 1 hour. The solid obtained was filtered and washed with acetone (100 ml). The product was dried at 55-60° C. under vacuum to obtain pure Form IV doxazosin mesylate (115-120 gms) which was characterized by XRD, IR and DSC. Purity according to HPLC: –99.89%.

Example 2

Preparation of Doxazosin Mesylate Form IV

Doxazosin mesylate (100 gms) was charged in methanol (1.0 lit) at room temperature. The contents were heated to reflux for 1 hour. The reaction mass was cooled to room temperature and stirred further for 1 hour. The product was isolated by vacuum filtration and dried under vacuum at 55-60° C. to obtain pure Form IV doxazosin mesylate (85 gms) which was characterized by XRD, IR and DSC. Purity according to HPLC: –99.91%.

Example 3

Comparative Intrinsic Dissolution Study

A tableting mixture (50 mg) comprising solely doxazosin mesylate (i.e. with no excipients) was prepared and compressed to a pellet using a manual hand press operating at a compression pressure of 5 tones for 5 minutes.

In-vitro dissolutions studies were performed on the 50 mg pellet in a LAB INDIA DISSO 2000.

The pellet was fixed in a PFTE holder, such that only the pellet surface came into contact with the dissolution medium. The PFTE loaded holder was placed in the dissolution vessel containing 900 ml of 0.01N HCl at 37±0.5° C. Three pellets were measured for each run of the design of the experiments. Stirring was performed with a paddle rotating at 50 rpm. The dissolution was followed up to 1440 min and the concentration of active ingredient, doxazosin mesylate, dissolved in the test medium was determined by removing samples of 10 ml at the specified time.

The concentration of doxazosin mesylate was quantified by HPLC UV method at a maximum wavelength of 245 nm under conditions as specified:
  Mobile Phase: 450:450:100:: Buffer:MeOH:Acetonitrile
  Buffer: 0.3% v/v Diethylamine. The pH adjusted to 2.5 with orthophosphoric acid
  Column: Inersil ODS 15 cm
  Flow: 1.0 ml/min The percentage of doxazosin mesylate released was plotted against time. The intrinsic dissolution rate was derived from the slope of this curve.

When compared with known forms of doxazosin mesylate, Form M and Form D, the new Form IV exhibited a superior rate of dissolution as shown in Table 2 below. The peak dissolution of 81.1% was achieved at 720 mins for the new Form IV; whereas, at the same time, 67.0% was achieved for form M and 74.5% for Form D.

Further, when compared with known Form D, which has the highest dissolution among the prior art forms, the new Form IV exhibited a higher dissolution rate by 8% at 30 minutes, 10.84% at 60 minutes, 15.14% at 120 minutes, 21.74% at 180 minutes and 29.33% at 240 minutes, and so on. This data is also shown graphically in FIG. 4.

TABLE 2

Intrinsic Dissolution Profile of Doxazosin Mesylate New Polymorph, Form IV with Prior Art Form D and Prior Art Form M

| Time in minutes | % Release of Doxazosin Mesylate Form -M | % Release of Doxazosin Mesylate Form -D | % Release of Doxazosin Mesylate Form -IV |
|---|---|---|---|
| 5 | 1.5 | 1.8 | 1.6 |
| 15 | 2.8 | 3.5 | 3.6 |
| 30 | 5.0 | 6.1 | 6.6 |
| 45 | 6.5 | 8.8 | 9.5 |
| 60 | 8.1 | 10.7 | 12.0 |
| 120 | 14.1 | 18.5 | 21.8 |
| 180 | 20.8 | 27.0 | 34.5 |
| 240 | 26.5 | 32.3 | 45.7 |
| 360 | 39.5 | 51.0 | 66.2 |
| 480 | 50.2 | 65.1 | 77.4 |
| 600 | 58.8 | 72.7 | 80.0 |
| 720 | 67.0 | 74.5 | 81.1 |
| 900 | 74.9 | 76.0 | 79.7 |
| 1080 | 78.0 | 75.8 | 79.2 |
| 1260 | 79.5 | 75.6 | 77.6 |

It will be appreciated that the invention may be modified within the scope of the appended claims.

The invention claimed is:

1. Crystalline Form IV of doxazosin mesylate, characterized by having an XRD pattern comprising peaks at 7.1, 11.8 and 13.9°2θ±0.2°2θ.

2. Crystalline polymorph Form IV of doxazosin mesylate according to claim 1, characterized by having an XRD pattern comprising further peaks at 17.3 and 23.7°2θ±0.2°2θ.

3. Crystalline polymorph Form IV of doxazosin mesylate according to claim 1, characterized by having an XRD pattern comprising peaks at 7.1, 9.3, 11.8, 13.9, 15.9, 22.3 and 24.2°2θ±0.2°2θ.

4. Crystalline Form IV of doxazosin mesylate according to claim 1, characterized by having an XRD pattern as shown in FIG. 1.

5. Crystalline Form IV of doxazosin mesylate according to claim 1, characterized by having an IR spectrum comprising characteristic IR spectra peaks at about 3345 cm$^{-1}$, 3185 cm$^{-1}$, 3033 cm$^{-1}$, 2934 cm$^{-1}$, 1660 cm$^{-1}$, 1635 cm$^{-1}$, 1597 cm$^{1}$, 1533 cm$^{-1}$, 1492 cm$^{-1}$, 1469 cm$^{-1}$, 1438 cm$^{-1}$, 1397 cm$^{-1}$, 1317 cm$^{-1}$, 1262 cm$^{-1}$, 1236 cm$^{-1}$, 1215 cm$^{-1}$, 1183 cm$^{-1}$, 1112 cm$^{-1}$, 1046 cm$^{-1}$, 989.9 cm$^{-1}$, 927 cm$^{-1}$, 869 cm$^{-1}$, 846 cm$^{-1}$, 819 cm$^{-1}$, 771 cm$^{-1}$, 756 cm$^{-1}$, 720 cm$^{-1}$, 663 cm$^{-1}$, 628 cm$^{-1}$, 575 cm$^{-1}$, 553 cm$^{-1}$, 522 cm$^{-1}$, 453 cm$^{-1}$ and 433 cm$^{-1}$±2 cm$^{-1}$.

6. Crystalline Form IV of doxazosin mesylate according to claim 1, characterized by having an IR spectrum as shown in FIG. 2.

7. Crystalline Form IV of doxazosin mesylate according to claim 1, characterized as having a DSC spectrum exhibiting a significant peak at around 258° C.

8. Crystalline Form IV of doxazosin mesylate according to claim 1, characterized by having a DSC spectrum as shown in FIG. 3.

9. Crystalline Form IV of doxazosin mesylate according to claim 1, characterized by having an intrinsic dissolution profile as shown in FIG. 4.

10. The process for preparing crystalline Form IV of doxazosin mesylate according to claim 1, comprising dissolving doxazosin base and methane sulfonic acid in a polar aprotic solvent, stirring the reaction mass for a period of time ranging from about 30 minutes to about 5 hours at a temperature ranging from about 25° C. to boiling point of the solvent, cooling the reaction mass to a temperature ranging from about 20° C. to 30° C. and stirring for a period of time ranging from about 30 minutes to about 2 days, and isolating the precipitated crystalline Form IV of doxazosin mesylate.

11. The process according to claim 10, wherein the doxazosine base is in any polymorphic form or in a mixture of any polymorphic forms.

12. The pharmaceutical composition comprising crystalline Form IV of doxazosin mesylate according to claim 1, together with one or more pharmaceutically acceptable excipients.

13. The pharmaceutical composition according to claim 12, which is in the form of a tablet suitable for oral delivery.

14. The method comprising utilizing crystalline Form IV of doxazosin mesylate according to claim 1 in treating hypertension or benign prostatic hyperplasia.

15. A method of treating hypertension or benign prostatic hyperplasia comprising administering to a patient in need thereof a therapeutically effective amount of crystalline Form IV of doxazosin mesylate according to claim 1.

* * * * *

UNITED STATES PATENT AND TRADEMARK OFFICE
CERTIFICATE OF CORRECTION

PATENT NO. : 8,383,627 B2
APPLICATION NO. : 12/810297
DATED : February 26, 2013
INVENTOR(S) : Kankan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 470 days.

Signed and Sealed this

First Day of September, 2015

Michelle K. Lee
*Director of the United States Patent and Trademark Office*